United States Patent
Kost et al.

(10) Patent No.: US 6,190,315 B1
(45) Date of Patent: Feb. 20, 2001

(54) SONOPHORETIC ENHANCED TRANSDERMAL TRANSPORT

(75) Inventors: Joseph Kost, Omer (IL); Samir S. Mitragotri, Cambridge; Robert S. Langer, Newton, both of MA (US)

(73) Assignee: Sontra Medical, Inc., Cambridge, MA (US)

( * ) Notice: Under 35 U.S.C. 154(b), the term of this patent shall be extended for 0 days.

(21) Appl. No.: 09/227,623

(22) Filed: Jan. 8, 1999

Related U.S. Application Data (60) Provisional application No. 60/070,813, filed on Jan. 8, 1998.

(51) Int. Cl.$^7$ .................................................. A61B 65/20
(52) U.S. Cl. ............................................. 600/309; 604/22
(58) Field of Search ................................ 604/20, 22, 49; 600/578, 573, 309; 601/2

(56) References Cited

U.S. PATENT DOCUMENTS

| | | |
|---|---|---|
| 3,551,554 | 12/1970 | Herschler . |
| 3,711,602 | 1/1973 | Herschler . |
| 3,711,606 | 1/1973 | Herschler . |
| 4,557,943 | 12/1985 | Rosler et al. . |
| 4,767,402 | 8/1988 | Kost et al. . |
| 5,165,418 | 11/1992 | Tankovich . |
| 5,445,611 | 8/1995 | Eppstein et al. . |
| 5,458,140 | 10/1995 | Eppstein et al. . |

FOREIGN PATENT DOCUMENTS

| | | |
|---|---|---|
| 9-202736 | 5/1997 | (JP) . |
| WO 97/04832 A1 | 2/1997 | (WO) . |
| WO 97/18851 A1 | 5/1997 | (WO) . |
| WO 98/00194 A2 | 1/1998 | (WO) . |

OTHER PUBLICATIONS

Bommer, et al., "Subcutaneous Erythropoietin," *Lancet* 2:406 (1988).

Burnette, "Iontophoresis" *Transdermal Drug Delivery Developmental Issues and Research Initiatives* (Hadgraft & Guy, Eds.), pp. 247–291,Marcel Kekker:New York, 1989.

Elias, "The Microscopic Structure of the Epidermis and Its Derivatives" in *Percutaneous Absorption: Mechanisms–Methodology–Drag Delivery* (Bronaugh & Maibach, Eds.), pp. 1–12 Marcel Dekker, New York, 1989.

Flynn, "Mechanism of Percutaneous Absorption from Physicochemical Evidence" in *Percutaneous Absorption: Mechanisms–Methodology–Drug Delivery* (Bronaugh & Maibach Eds.), pp. 27–51 Marcel Dekker:New York, 1989.

Friedman, *Interferons: A Primer*, Academic Press: New York, 1981.

Grups & Frohmüller, "Cyclic Interferon Gamma Treatment of Patients with Metastatic Renal Carcinoma," *Br. J. Urology* 64(3):218–220 (1989).

Junginger, et al., "Visualization of Drug Transport Across Human Skin and the Influence of Penetration Enhancers," in *Drug Permeation Enhancement* (Hsieh, Ed.), pp. 59–89, Marcel Dekker, Inc.:New York, 1994.

Kost & Langer, "Ultrasound–Mediated Transdermal Drug Delivery" in *Topical Drug Bioavailability Bioequivalence and Penetration* (Maibach & Shah, Eds.), pp. 91–104, Plenum Press:New York, 1993.

Krall, et al., *World Book of Diabetes in Practice* Elsevier: Amsterdam, 1988.

Levy, et al., "Effect of Ultrasound on Transdermal Drug Delivery to Rats and Guinea Pigs," *J. Clin. Invest.* 83:2074–2078 (1989).

Parkin, et al., "Atopic manifestations in the acquired immune deficiency syndrome: response to recombinant interferon gamma," *Br. Med. J.* 294:1185–1186 (1987).

Prausnitz, et al., "Electroporation of mammalian skin: A mechanism to enhance transdermal drug delivery," *Proc. Natl. Acad. Sci. USA* 90:10504–10508 (1993).

Tamada, et al., "Measurement of glucose in diabetic subjects using noninvasive transdermal extraction," *Nature Med.* 1:1198–1201 (1995).

Walters, "Penetration enhancers and their use in transdermal therapeutic systems" *Transdermal Drug Delivery: Development Issues and Research Initiatives* (Hadgraft and Guy, eds.) pp. 197–246, Marcel Dekker:New York, 1986.

Waynforth, *Experimental and surgical technique in the rat* (2$^{nd}$ Ed.) pp. 215–222, Academic Press:London, (1992).

*Primary Examiner*—Eric F. Winakur
*Assistant Examiner*—Joseph Cadugan
(74) *Attorney, Agent, or Firm*—Arnall Golden & Gregory, LLP (57) ABSTRACT

Methods for enhanced transdermal transport wherein the application of ultrasound is required only once for repeated or sustained transdermal extraction or delivery, over a period of time, rather than prior to each extraction or delivery. The method is applicable to analyte extraction, as well as for drug delivery. The method involves the initial application of an amount of low frequency ultrasound effective to permeabilize the skin or membrane followed by analyte extraction or drug delivery over a period of time. The initial application of ultrasound is effective to permeabilize the skin or membrane for at least about 30 minutes, preferably at least one to two hours, and more preferably up to four to ten hours. The ultrasound is preferably low frequency ultrasound, less than 2.5 MHz, more preferably less than 1 MHz. The transdermal transport can be enhanced by the application of a secondary driving force such as suction, osmotic pressure gradient, concentration gradient, iontophoresis, electroporation, magnetic field, additional ultrasound, or mechanical pressure.

13 Claims, 5 Drawing Sheets

SONOPHORETIC ENHANCED TRANSDERMAL TRANSPORT

CROSS REFERENCE TO RELATED APPLICATION

Priority is claimed to provisional application Serial No. 60/070,813, filed on Jan. 8, 1998, entitled "Sonophoretic Transdermal Analyte Extraction" by Joseph Kost, Samir S. Mitragotri, and Robert S. Langer.

FIELD OF THE INVENTION

The present invention generally relates to improved methods for transdermal transport using ultrasound. More specifically, methods are provided enabling repeated analyte extraction or dug delivery over a period of time following a single application of low frequency ultrasound.

BACKGROUND OF THE INVENTION

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, in *Percutaneous Absorption: Mechanisms-Methodology-Drug Delivery*, Bronaugh, R. L. et al. (Eds), pages 1–12, Marcel Dekker, New York (1989).

The skin is a complex structure. There are at least four distinct layers of tissue: the nonviable epidermis (stratum corneum, SC), the viable epidermis, the viable dennis, and the subcutaneous connective tissue. Located within these layers are the skin's circulatory system, the arterial plexus, and appendages, including hair follicles, sebaceous glands, and sweat glands. The circulatory system lies in the dermis and tissues below the dennis. The capillaries do not actually enter the epidermal tissue but come within 150 to 200 microns of the outer surface of the skin. The highly-ordered structure of the lipid bilayers confers an impermeable character to the SC (Flynn, G. L., in *Percutaneous Absorption: Mechanisms-Methodology-Drug Delivery*; Bronaugh, R. L. et al. (Eds.), pages 27–53, Marcel Dekker, New York, (1989). The word "transdermal" is used herein as a generic term. However, in actuality, transport of drugs occurs only across the epidermis where the drug is absorbed in the blood capillaries. In comparison to injections, TDD can reduce or eliminate the associated pain and the possibility of infection.

Several methods have been proposed to enhance transdermal drug transport, including the use of chemical enhancers, ie. the use of chemicals to either modify the skin structure or to increase the drug concentration in a transdermal patch (Burnette, R. R., in *Developmental Issues and Research Initiatives*; Hadgraft J., et al. (Eds.), pages 247–288, Marcel Dekker, New York (1989); Junginger, et al. in *Drug Permeation Enhancement*; Hsieh, D. S., (Eds.), pages 59–90; Marcel Dekker, New York (1994)) and the use of applications of electric fields to create transient transport pathways [electroporation] or to increase the mobility of charged drugs through the skin [iontophoresis] (Prausnitz, Proc. Natl. Acad. Sci. USA 90: 10504–10508 (1993); Walters, K. A., in *Transdennal Drug Delivery: Developmental Issues and Research Initiatives*, Hadgraft J., Guy, R. H., (Eds.) Marcel Dekker, New York (1989)). Another approach that has been explored is the application of ultrasound.

Ultrasound has been shown to enhance transdermal transport of low-molecular weight drugs (molecular weight less than 500) across human skin, a phenomenon referred to as sonophoresis (Levy, J. Clin. Invest. 1989, 83, 2974–2078; Kost and Langer in "*Topical Drug Bioavailability, Bioequivalence, and Penetration*"; pp. 91–103, Shah V. P., M. H. I., Eds. (Plenum: New York, 1993); Frideman, R. M., "*Interferons: A Primer*", Academic Press, New York, 1981). Although a variety of ultrasound conditions have been used for sonophoresis, the most commonly used conditions correspond to therapeutic ultrasound (frequency in the range of between one MHz and three MHz, and intensity in the range of between above zero and two W/cm$^2$) (U.S. Pat. No. 4,767,402 to Kost, et al.). It is a common observation that the typical enhancement induced by therapeutic ultrasound is less than ten-fold. In many cases, no enhancement of transdermal drug transport has been observed upon ultrasound application. U.S. Pat. Nos. 5,458,140 and 5,445,611 to Eppstein et al. disclose the use of ultrasound at a frequency range of between 0.1 and 100 MHz, preferably between 3 and 30 MHz, in combination with chemical enhancers, to enhance skin permeability. The ultrasound was frequency, intensity and/or phase modulated. An increase in permeability was noted during application of the ultrasound but decreased to passive diffusion rates when ultrasound was discontinued (see Example 4 in both patents).

U.S. Pat. No. 5,323,769 to Bommannan discloses ultrasound enhanced delivery of molecules into and through the skin, in combination with chemical permeation enhancers. The ultrasound is applied at frequencies above 10 MHz. The ultrasound must be applied "relatively simultaneously" with the molecules being delivered, within at least six minutes, preferably within two minutes.

Application of low frequency (between approximately 20 and 200 kHz) ultrasound can dramatically enhance transdermal transport of molecules when applied directly to the drug or at the time of collection, as described in WO 97/04832 by Massachusetts Institute of Technology. Transdermal transport enhancement induced by low-frequency ultrasound was found to be as much as 1000-fold higher than that induced by therapeutic ultrasound.

There is a major medical need to extract analytes through the skin, such as in diabetes where it is desirable to measure blood glucose several times per day in order to optimize insulin treatment and thereby reduce the severe long-term complications of the disease. Currently, diabetics do this by pricking the highly vascularized fingertips with a lancet to perforate the skin, then milking the skin with manual pressure to produce a drop of blood, which is then assayed for glucose using a disposable diagnostic strip and a meter into which this strip fits. This method of glucose measurement has the major disadvantage that it is painful, so diabetics do not like to obtain a glucose measurement as often as is medically indicated.

Therefore, many groups are working on non-invasive and less invasive means to measure glucose, such as micro lancets that are very small in diameter, very sharp, and penetrate only to the interstitium (not to the blood vessels of the dermis). A small sample, from about 0.1 to two $\mu$l, of interstitial fluid is obtained through capillary forces for glucose measurements. Other groups have used a laser to breach the integrity of the stratum comeum and thereby make it possible for blood or interstitial fluid to diffuse out of such a hole or to be obtained through such a hole using pneumatic force (suction) or other techniques. An example of such a laser based sampling device is disclosed in U.S. Pat. No. 5,165,418 to Tankovich and WPI ACC No: 94-167045/20 by Budnik (assigned to Venisect, Inc.).

It would be of significant utility to be able to obtain a sample of blood, lymph, or interstitial fluid more quickly, using an easier procedure, and relatively noninvasively. It would also be advantageous to be able to repeatedly extract analyte or deliver drug transdermally over a period of time.

It is an object of the present invention to provide methods enabling repeated or continuous transdermal transport with minimal effort to permeabilize the skin.

SUMMARY OF THE INVENTION

Methods are described wherein the application of ultrasound is required only once for repeated or sustained transdermal extraction or delivery, over a period of time, rather than prior to each extraction or delivery. Examples demonstrate multiple sample extractions could be obtained over a time period of up to ten hours after a single ultrasound application to the collection site. The method is applicable to extraction of analyte, such as glucose, extraction, as well as for drug delivery. The method may also be applicable for enhancing permeation of cellular membranes.

In the preferred embodiment, low frequency ultrasound effective to permeabilize the skin or membrane is applied initially, alone or in combination with an enhancer followed by mechanical analyte extraction or drug delivery over a period of time. The initial application of ultrasound is effective to permeabilize the skin or membrane for at least about 30 minutes, preferably at least one to two hours, and more preferably up to four to ten hours. The transdermal transport can be enhanced by the simultaneous or subsequent application of a secondary driving force such as chemical permeability or transport enhancers, suction, capilary forces, convection, osmotic pressure gradient, concentration gradient, iontophoresis, electroporation, magnetic field, additional ultrasound, or mechanical pressure.

DETAILED DESCRIPTION OF THE INVENTION

I. Definitions

Ultrasound is defined as sound at a frequency of greater than about 20 kHz. Therapeutic ultrasound is typically between 20 kHz and 3 MHz, more typically between 750 kHz and 3 MHz.

Sonophoresis is defined as the application of ultrasound to the skin resulting in enhanced transdermal transport of molecules.

Low frequency sonophoresis or ultrasound is defined as sonophoresis or ultrasound at a frequency that is less than 2.5 MHz, more typically less than 1 MHz, more preferably in the range of 20 to 100 kHz.

Analyte is defined as a molecule present in the body, particularly in the blood, interstitial fluid, lymph, or intercellular fluid, which can include a drug administered to an individual by any means as well as endogenous molecules.

Analyte extraction is defined as the removal of analyte from the body, a transport completely or partially through the skin, typically in blood, lymph, interstitial fluid, or intercellular fluid. Removal may be after analyte has passed through the skin or may be removal from within the skin, where the methods facilitate partial movement of analyte into or through the skin. The term through as used herein means.

Drug is defined as a therapeutic, prophylactic, or diagnostic molecule or agent, and can be in a form dissolved or suspended in a liquid, a solid, or encapsulated and/or distributed in or within micro or nano particles, emulsions, liposomes or lipid vesicles.

Drug delivery is defined as the delivery of a drug into blood, lymph, interstitial fluid, a cell or tissue.

Transdermal transport is defined as movement of analyte into or through the skin or delivery of drug into or through the skin. Membrane and skin are used interchangeably herein and include skin, cellular membranes, organs, and tissues, as well as other biological surfaces.

Transdermal patch is an externaly applied device for delivery or extraction of molecules into or through the skin.

Driving force means a chemical or physical treatment that alters movement of an analyte or drug into or through the membrane.

II. Methods of Enhanced Transport

In general, the method includes the steps of 1) applying low frequency ultrasound to skin or tissue for a time and at a frequency and voltage effective to permeabilize the area where transport is desired, over a period of time from 30 minutes up to ten hours for a time sufficient to permeabilize the skin; and 2) extracting analyte or delivering drug into or through the skin continuously or repeatedly over the time the skin is permeabilized. The method may further include repermeabilizing the skin over the period of time during which transport or extraction occurs. The method may further include using chemical or physical enhancers to enhance transport.

Permeabilization

Ultrasound is preferably administered at frequencies of less than or equal to about 2.5 MHz, preferably at a frequency that is less than one MHz, more typically in the range of 20 to 100 kHz. Exposures are typically for between 20 seconds and 10 minutes, continuously, but may be shorter and/or pulsed, for example, 100 to 500 msec pulses every second for a time sufficient to perneabilize the skin. The ultrasound intensity should be at a level that preferably does not raise the skin temperature more than about one to two degrees Centigrade or cause permanent damage to the skin, under the conditions and with the particular device to be used. This typically will be less than 20 W/cm$^2$, preferably less than 10 W/cm$^2$. The intensity and time of application are inversely proportional, so that higher intensities should be applied for shorter periods of time, in order to avoid skin damage. It should be understood that although the normal lower range of ultrasound is 20 kHz, one could achieve comparable results by varying the frequency to less than 20 kHz, that is, into the sound region down to about one kHz. The time needed is dependent upon the frequency and intensity of the ultrasound and the skin condition. At 20 kHz, for example, at an intensity of 10 mW/cm$^2$, and a duty cycle of 50%, skin on a human forearm is sufficiently permeabilized in about five minutes.

Permeabilizing ultrasound can be applied for a predetermined amount of time or can be applied only until permeabilization is attained. Since skin conditions can change over time, based on aging, diet, stress, and other factors, it may be preferable to measure permeability as ultrasound is applied to ensure sufficient ultrasound is applied and to minimize the risk of skin damage. Several methods can be used to determine when sufficient permeabilization has been reached. One way is to measure relative skin conductivity at the permeabilization site versus a reference point. These measurements are performed by applying a small AC or DC electric potential across two electrically isolated electrodes in contact with skin. The electric current flowing through these electrodes is measured using an ammeter and the skin resistance is measured using the values of the potential and the current.

Another way to determine when sufficient permeabilization has been reached is to measure absolute conductivity. Fully permeabilized skin should have a resistance of no more than about 5 kohms in most situations. Another method is to detect and/or quantitate the transdermal movement of an analyte such as creatinine or calcium that is present in interstitial fluid in a fairly constant amount, which can be used either to calibrate the concentration of analyte to be extracted and quantitated, or used as a measure of permeability—i.e., the higher the concentration of constant analyte, the greater the degree of permeabilization. The degree of permeability can also be monitored using a sensor that determines the concentration of the drug being delivered or analyte being extracted. As the permeability decreases, the drug concentration will decrease, and vice versa.

The skin is preferably permeable for at least 30 minutes, preferably at least an hour, or two hours. Under some conditions, the skin may remain permeable for up to eight to ten hours. It may be desirable to repermeabilize the skin with another dose of permeabilizing ultrasound under the same, or different conditions.

Several methods may be useful to attain or maintain permeabilization for an extended period of time. Cavitation enhancers, as described more fully below can be used. The chemical and physical enhancers and driving forces described below may also act to keep the skin permeable. In addition, large molecules such as sodium lauryl sulfate, for example, may permeate the skin and serve as spacer molecules to keep the skin open.

Site of Administration

The ultrasound is preferably administered to the skin or at a site selected based on convenience to the patient as well as maximum drug or analyte penetration. For example, the arm, thigh, and stomach represent areas of relatively thin skin and high surface area, while the hands and feet are uneven and callused. In the preferred embodiment, ultrasound is applied first to increase the permeability of the skin and then drug is applied to the site where it diffuses through the skin or is otherwise transported through the skin.

A typical daily erythropoeitin dose given subcutaneously to anemic patients is about 400 U (cited in 'Subcutaneous Erythropoeitin, Bommer J., Ritz E., Weinreich T., Bommer G., Ziegler T., Lancet, 406, 1988). If this dose was to be delivered in three steps, each involving application over one hour, the transdermal flux required would be about 140 U/hour. If the dosage was to be delivered continuously over a period often hours, the required flux rate is 40 U/hour. One unit of erythropoeitin corresponds approximately to 7.6 nanograms of erythropoeitin.

III. Molecules to be Transported

The methods can be used to detect and monitor analyte, such as glucose, levels. The methods can also be used to deliver drugs, such as insulin. The methods can be used to enhance or cause the transport of different consumer products. For example, the methods can be used to increase the transport of dyes and other substances of interest to hair to get a faster/sturdier and also longer effect. The methods can be used for impregnating substances into and coloring of fabrics, wood, leather, fibers, etc. Other indications include promoting faster food marination, enhancing the pearl culturing process, increasing the penetration of molecules that would treat skin conditions such as for the treatment of cellulite, psoriatic plagues, and scars. Other indications include application of ultrasound for cell culture, fermentation to enhance the growth, proliferation and/or secretion of cellular products that are of interest.

Drug Delivery

Drugs to be administered or measured as analytes include a variety of bioactive agents, including proteins and peptides. Specific examples include insulin, erythropoietin, and interferon. Other materials include nucleic acid molecules such as antisense and genes encoding therapeutic proteins, synthetic organic and inorganic molecules including anti-inflammatories, antivirals, antifungals, antibiotics and local anesthetics, and saccharides and polysaccharides. The drug will typically be administered in an appropriate pharmaceutically acceptable carrier having an absorption coefficient similar to water, such as an aqueous gel, ointment, lotion, or suspension. Alternatively, a transdermal patch can be used as a carrier. It may be desirable to include protease inhibitors with protein and peptide drugs to minimize protease activity. Molecules for skin treatment such as retinoids, dyes, and vitamin D.

In one embodiment, the drug is in the form of or encapsulated in a delivery device such as a liposome, lipid vesicle, emulsion or polymeric nanoparticles, microparticle, microcapsule, or microspheres (referred to collectively as microparticles unless otherwise stated). These can be formed of polymers such as polyhydroxy acids, polyorthoesters, polyanhydrides, and polyphosphazenes, or natural polymers such as collagen, polyamino acids, albumin and other proteins, alginate and other polysaccharides, and combinations thereof. The microparticles can have diameters of between 0.001 and 100 microns, although a diameter of less than 10 microns is preferred. The microparticles can be coated or formed of materials enhancing penetration, such as lipophilic materials or hydrophilic molecules, for example, polyalkylene oxide polymers, and conjugates, such as polyethylene glycol.

The ultrasound should be applied to an area of skin approximately equal to the size of the application device. For example, the surface of a transdennal Fentanyl™ patch [ALZA Corporation] is 40 cm$^2$, so ultrasound should be administered to a surface area of 40 cm$^2$.

The required application regime for treatment of a patient can be calculated based on the recommended dosage of the drug and the flux rate of the drug. A typical diabetic patient (70 Kg weight) takes about 12 Units of insulin three times a day (total dose of about 36 Units per day: cited in 'World Book of Diabetes in Practice' Krall, L. P. (Ed), Elsevier, 1988). If each insulin dose is to be delivered by sonophoresis over one hour, the required transdermal flux is 12 U/hour. Note that one unit (one U) of insulin corresponds approximately to 40 mg of insulin. Insulin is commercially available as a solution [Humulin™] of 100 U/ml.

A typical γ-interferon dose given each time to patients suffering from cancer or viral infections is about 5×10$^6$ U (Grups J. W., Frohmuller H. G., Br. J. Med., 1989, 64 (3) 218–220; Parkin J. M., Eales L., Galazka A., Pinching A., Br. Med. J., 1987, 294: 1185–1186) Similar doses of αinterferon and β-interferon have also been shown to enhance the immune response of patients suffering from viral infections and cancer (cited in 'Clinical Applications of interferons and their inducers', Ed. Stringfellow D., Marcel Dekker, New York, 1986). If this interferon dose was to be given over one hour, the required transdermal flux would be 5×10$^6$ U/hour. Note that one unit of γ-interferon corresponds approximately to one pg of γ-interferon.

Analytes

A variety of analytes are routinely measured in the blood, interstitial fluid and/or lymph. Examples of typical analytes that can be measured include blood sugar (glucose), cholesterol, bilirubin, creatinine, vitamin K or other clotting factors, uric acid, carcinoembryonic antigen or other tumor antigens, and various reproductive hormones such as those associated with ovulation or pregnancy. Other analytes that can be measured include alcohol and drugs.

In general, analyte extraction is preceded by application of ultrasound to permeabilize the skin. Analyte is then collected as it diffuses or is otherwise transported through the skin. In many cases, it will be desirable to apply vacuum to the permeabilized skin. In other cases, it will be desirable to apply vacuum and/or additional driving forces as further described below. The analyte can be collected in a reservoir placed on the skin, which may include a collection material, such as a liquid or gel. In some embodiments, the analyte can be collected directly into a collection medium that detects for the presence and/or amount of the analyte.

The method can also be used to draw analyte closer to the skin surface, rather than extracting the analyte from the skin, so that the analyte can be measured. For example, noninvasive in vivo measurement of glucose has been proposed using near-infrared spectroscopy. However, the penetration depth of near infrared is not sufficient for reliable measurements. The method described herein can be used to extract glucose to near the skin surface where it can be measured.

IV. Transport Enhancers

Transdermal transport enhancers that can be applied before, during or after the permeabilizing ultrasound include physical driving forces and chemical enhancers or driving forces.

Surfactants and Other Chemical Enhancers and Driving Forces

Chemical enhancers include lipid bilayer disrupting agents and solubility enhancers. Chemical enhancers have been found to increase drug transport by different mechanisms. Chemicals that enhance permeability through lipids are known and commercially available. For example, ethanol has been found to increase the solubility of drugs up to 10,000-fold and yield a 140-fold flux increase of estradiol through the skin, while unsaturated fatty acids have been shown to increase the fluidity of lipid bilayers. Examples of fatty acids that disrupt lipid bilayer include linoleic acid, capric acid, lauric acid, and neodecanoic acid, which can be in a solvent. Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones).

Other chemical enhancers, not necessarily associated with binary systems, include dimethylsulfoxide (DMSO) or aqueous solutions of DMSO such as those described in U.S. Pat. No. 3,551,554 to Herschler; U.S. Pat. No. 3,711,602 to Herschler; and U.S. Pat. No. 3,711,606 to Herschler, and the azones (n-substituted-alkyl-azacycloalkyl-2-ones) such as noted in U.S. Pat. No. 4,557,943 to Coope.

Surfactants can act as solubility enhancers for some drugs as well as permeability enhancers by fluidizing the lipid bilayer. A preferred surfactant is sodium lauryl sulfate (SLS) present in an amount of about 0.25 to 5%, preferably about 1%. Other useful surfactants include fatty acids, fatty alcohols, esters of fatty acids, alkyl sulfonates, sodium salts of sulfonic acid, alkyl sulfonic acid, Tween™, Spam™, and pluronics™, typically in a concentration in the range of 0.25 to 5% weight/volume.

Physical Enhancers

Physical driving forces include suction, osmotic pressure gradient, concentration gradient, iontophoresis, electroporation, magnetic fields, additional ultrasound, and mechanical pressure.

Physical driving forces are preferably applied after the initial permeabilizing ultrasound to enhance transport of analyte or drug into or through the skin or tissue. The driving force can be applied continuously over a period of time or at intervals during the period of permeabilization.

Mechanical pressure can be positive pressure or negative pressure, such as a vacuum. Suction may induce convective transport across the skin, thus enhancing the effect of ultrasound on transdermal transport.

Osmotic pressure gradients can be applied using salts (for example, 2 M NaCl) or sugars such as mannitol (1 M solution in saline) and dextrans.

Application of electric current enhances transdermal transport by different mechanisms. First, application of an electric field provides an additional driving force for the transport of charged molecules across the skin (electrophoresis) and second, ionic motion due to application of electric fields may induce convective flows across the skin, referred to as electrosmosis. This mechanism is believed to play a dominant role in transdermal transport of neutral molecules during iontophoresis. Iontophoresis involves the application of an electrical current, preferably DC, or AC, at a current density of greater than zero up to about 1 mA/cm$^2$. Typically, a constant voltage is applied since resistance changes over time, usually in the range of between greater than zero and four volts.

Application of magnetic fields to the skin pretreated with ultrasound may also result in a higher transport of magnetically active species across the skin. For example, polymer microspheres loaded with magnetic particles could be transported across the skin using sonophoresis and magnetic fields.

Additional ultrasound can be applied at higher, lower, or the same frequency as the initial permeabilizing ultrasound. In other cases, it may be preferable to use lower frequency, "maintenance" doses of ultrasound to keep the skin permeabilized.

Cavitation Enhancers

Greater transdermal transport can be achieved by inducing cavitation either inside or outside of the skin. Cavitation is the growth and oscillations of air bubbles present in fluids and air pockets present in the keratinocytes of the SC. Application of low-frequency ultrasound appears to induce cavitation inside as well as outside the skin and disorganize the SC lipid bilayers thereby enhancing transdermal transport. In addition, oscillations of cavitation bubbles may result in significant water penetration into the disordered lipid regions and may cause the formation of aqueous channels through the intercellular lipids of the SC. This allows transport of permeants across the disordered lipid domains, then across keratinocytes and the entire SC. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (by a factor of up to 25) than that through the tortuous intercellular lipids in the case of passive transport.

Cavitation can be enhanced by providing nuclei in the form of gas bubbles, crevices, or particulate. Examples of cavitation enhancers include flourocarbons, particulate matter (for example, microspheres, silica, titanium dioxide particles, polymer particles), gases (for example, argon, air), and stabilized air bubbles.

Occurrence of cavitation on the skin surface may also be enhanced by coating the skin surface with a wetting agent in the entire area of application of ultrasound except for a spot. Cavitation may preferentially occur at the spot due to the difference in wetting properties of the skin and the coating. The coating may be made from a polymer such as poly (methyl methacrylate) or it may be a membrane made from poly(vinyl difluoride), for example.

V. Devices for Transdermal Transport

The ultrasound device preferably includes a transducer and a portable or bench-top ultrasound generator. The ultrasound generator also may include circuitry for measurement of skin resistance and/or analyte concentration and display of the measured analyte concentration. The transducer is placed against or near the skin and ultrasound is activated for a defined period of time. Subsequent application of chemical enhancers or physical driving forces can be applied using the same device or a separate device. Extracted analytes can be collected in the device or, preferably, in a smaller collection reservoir, such as a patch. Drugs can be delivered from the device or, preferably, from a drug reservoir, such as a patch.

Ultrasound Channeling or Focusing

Transdermal transport enhancement induced by ultrasound increases with increasing ultrasound pressure amplitude. However, application of high ultrasound pressure amplitudes is prohibited by the discomfort associated with it. The extent of discomfort induced by ultrasound increases with increasing application area, probably due to exposure of more pain receptors to ultrasound. Application of high energy ultrasound to a small area may avoid excessive pain and provide optimal conditions for transdermal analyte extraction or drug delivery. It is possible to achieve application of ultrasound to a small area using geometric channeling or using a vibrating element as described in WO 98/00194 by Sontra. Alternatively, in some cases, particularly drug delivery, it may be preferable to apply the drug to a larger skin surface area, in which case diffuse ultrasound would be preferred.

The Transducer

The transducer is preferably operated at a frequency in the range of between 20 kHz and 2.5 MHz using appropriate electrical signal generators and amplifiers. The transducer more preferably is operated at a frequency in the range of between 20 and 100 kHz. Other ultrasound parameters including, but not limited to, amplitude, duty cycle, distance from the skin, and application time may be varied to achieve sufficient enhancement of transdermal transport. The intensity preferably varies from zero to 20 W/cm$^2$. The duty cycle can vary from between one and 100%. The transducer can be positioned at a distance from the skin between 0.1 and 10 mm. The application time preferably ranges between 20 seconds and five minutes.

Coupling Medium

The ultrasound is typically applied through a cavity filled with an aqueous or non-aqueous coupling medium. The coupling medium increases the efficient transfer of ultrasound energy from transducer to the skin. Appropriate mixtures of these coupling media may also enhance cavitation activity near the skin or inside the skin, increasing permeability and effectiveness of transport of molecules into or across the skin. The coupling medium can also serve as the analyte extraction or drug delivery medium, or may be removed before analyte extraction or drug delivery.

The coupling medium can include, but is not limited to, water, saline, alcohols including ethanol and isopropanol (in a concentration range of 10 to 100% in aqueous solution), surfactants such as Triton X-100, SLS, or SDS (preferably in a concentration range of between 0.001 and 10% in aqueous solution), DMSO (preferably in a concentration range of between 10 and 100% in aqueous solution), fatty acids such as linoleic acid (preferably in a concentration range of between 0.1 and 2% in ethanol-water (50:50) mixture), azone (preferably in a concentration range of between 0.1 and 10% in ethanol-water (50:50) mixture), polyethylene glycol in a concentration range of preferably between 0.1 and 50% in aqueous solution, histamine in a concentration range of preferably between 0.1 and 100 mg/ml in aqueous solution, EDTA in a concentration range of preferably between one and 100 mM, sodium hydroxide in a concentration range of preferably between one and 100 mM, and combinations thereof.

In the case of drug delivery, the coupling medium also contains a drug that is transported across the skin by diffusion or other driving forces including convection and iontophoresis.

The coupling medium can also include a chemical enhancer. Transport enhancement may be obtained by adding capillary permeability enhancers, for example, histamine, to the coupling medium. The concentration of histamine in the coupling medium may be in the range of between 0.1 and 100 mg/ml. These agents may be delivered across the epidermis during application of ultrasound and may cause local edema that increases local fluid pressure and may enhance transport of analytes across the skin. In addition, the occurrence of free fluid due to edema may induce cavitation locally so as to enhance transport of analytes as well as drugs across the skin.

Sensor

The device may include an integrated sensor, such as a chemical sensor, biosensor, or other measurement system to form a complete extraction/measurement system. The unit can be constructed to function as a closed loop drug delivery unit, including drug delivery means, analyte recovery means, sensing means to measure the analyte, and control means to provide a signal to the drug delivery means. In a preferred embodiment, the unit would include subunits to withdraw fluid and calculate the concentration of glucose, for example, determine the amount of insulin needed, and deliver that amount of insulin.

The device can include means for assaying the amount of analyte extracted or amount or rate of drug delivery. For example, an assay method that results in a color change could be used. The change in color could be detected using a light beam that enters into a disposable chamber through a window on top. The analyte may also be detected in the chamber through the use of an enzyme electrode or biosensor. The analyte sensing system can consist of enzymes that react with the analyte of interest and either electrochemical or optical transducers that measure the content of reaction. Examples of such enzymes are glucose oxidase and glucose dehydrogenase.

An example of an enzyme electrode for glucose is a screen-printed electrode on the surface of which is immobilized glucose oxidase and an electron mediator such as ferrocene or its derivatives. Electrons generated by the oxidation of glucose are transferred from glucose oxidase to the electrode via the mediator. Thus, the concentration of glucose in the analyte solution is proportional to the current generated. Yet another detection mechanism may be used based on near-infrared spectroscopy. In this method, concentration of extracted glucose in a gel is detected by the absorption of the near-infrared light that passes through the chamber through two windows. The window through which the light passes may be separate from the ultrasound transducer or the beam may pass directly through the transducer.

Calibration of the assay means can be accomplished using the concentration of a second analyte. The primary analyte can be normalized, lowering extraction to extraction and site to site variability, by the concentration of the second analyte.

Examples of the secondary analyte include, but are not limited to, salts, creatinine, cholesterol, and triglycerides. Measurements of salts include specific ion measurements such as $Na^+$ or $Ca^{2+}$ or overall ion-measurements using solution conductivity. Normalization may be a linear or non-linear relationship.

Indications

Of special interest is the application of ultrasound for regenerative medicine for skin, organs and other tissues and in tissue engineering where the cells are cultured on carriers and transport properties are of importance.

EXAMPLE 1

Extraction and Measurement of Glucose

Seven volunteers, four males and three females from 18 to 40 years of age, diagnosed with type 1 diabetes mellitus for between 1 and 20 years, without peripheral vascular disease or other known diabetic complications, participated in this study. Subjects were admitted to the clinical research center and instructed to follow their usual daily mean and insulin injection regimen.

A glass chamber (approximately 1.5 cm$^2$ in area) was placed on the forearm, secured in place with an elastic strap, and filled with 1 ml of sterile saline. An indwelling catheter was introduced in the other forearm for removing blood samples for repeated blood glucose analysis. At the end of 1 hour, the saline was removed from the chamber and filled with 2 ml of 1% sodium lauryl sulfate (SLS) in saline. Ultrasound (20 kHz, 11 $\mu$m tip displacement, pulsed for 5 seconds on/5 seconds off) was applied to the chamber. The ultrasound transducer (1 cm diameter) was placed at distance of 1 cm from the skin and was activated for up to 2 minutes. The SLS solution was then replaced with 0.5 ml of saline. Ultrasound was applied only once for less than 2 minutes prior to the four hours of intermittent vacuum extractions. Vacuum (10 in Hg) was applied to the chamber for 5 minutes for each extraction and was repeated twice every 30 minutes. At the end of each vacuum application, the solution in the chamber was removed for glucose measurement and the chamber was refilled with 2 ml saline, and covered using parafilm prior to the next vacuum application. The samples from the chamber taken during vacuum applications were assayed for glucose (Sigma 315 kit). Samples (2.5 ml) were taken from the venous catheter to measure blood glucose concentration. One hour after the ultrasound application a controlled meal (240 ml Sustacal™) was given to increase blood glucose levels. The sampling procedure was repeated for an additional 4 hours. At the end of the experiment, patients were given a personal interview regarding comfort issues related to sonophoretic analyte monitoring. Four subjects returned after two days to have the skin that had been exposed to ultrasound reevaluated, and the other patients were interviewed by telephone.

Figure 1:
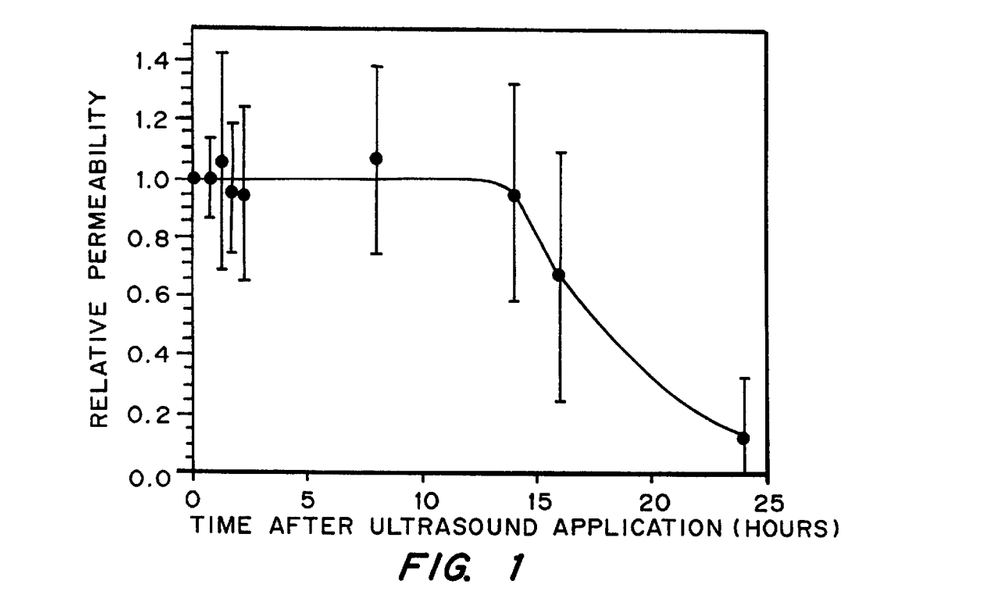
FIG. 1, illustrating skin permeability recovery after ultrasound application, is a graph comparing relative permeability to time after initial ultrasound application (hours). The measurements were performed on four healthy volunteers (2–3 sites on each subject) and seven type I diabetic volunteers (at a single site on each subject). Data shows average permeability (±standard deviation) on all sites on all subjects.

Skin permeability was measured at a single site (mid volar forearm) after ultrasound application. The results are shown in FIG. 1. The average skin permeability varied from subject to subject, from $1.3 \times 10^{-3}$ ($\pm 9.6 \times 10^{-4}$) cm/hr to $1.8 \times 10^{-2}$ ($\pm 1.4 \times 10^{-3}$) cm/hr. However, the time variation of these permeabilities at a given site for a given subject over a period of four hours was within 20% (a standard deviation commonly observed in existing glucose measurement methods). The skin permeability remained high for about 15 hours and decreased to its normal value by 24 hours.

Figure 2:
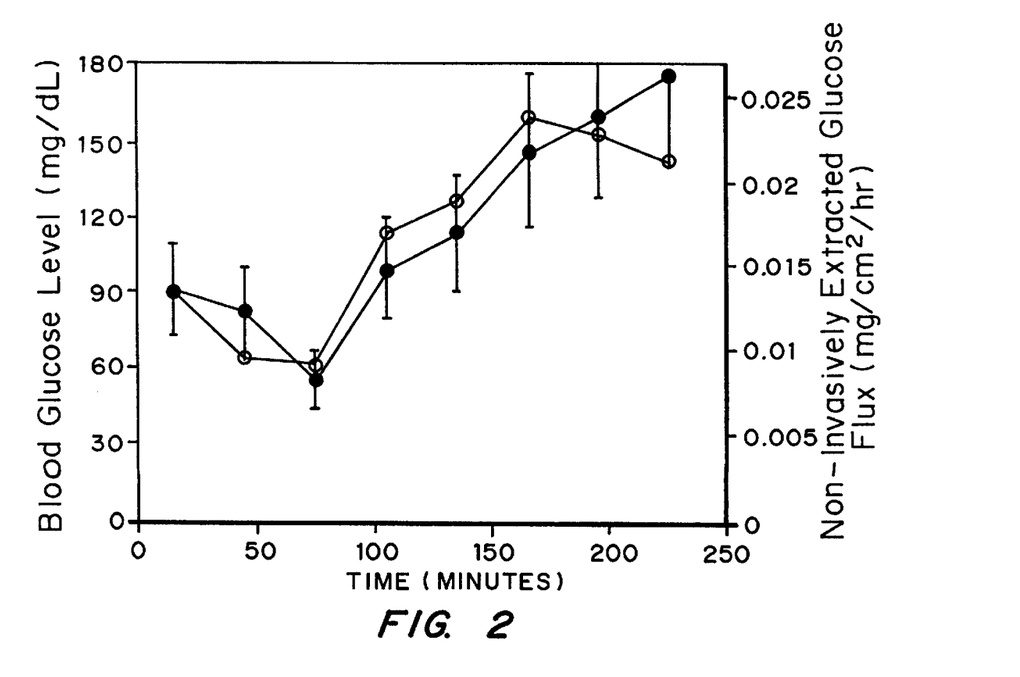
FIG. 2, is a graph comparing blood glucose levels (mg/dL) and glucose flux (mg/cm$^2$/hr) over a 250 minute period of time, where (○) is blood concentration and (●) is glucose flux. Error bars indicate typical error in fluxes.
Figure 3:
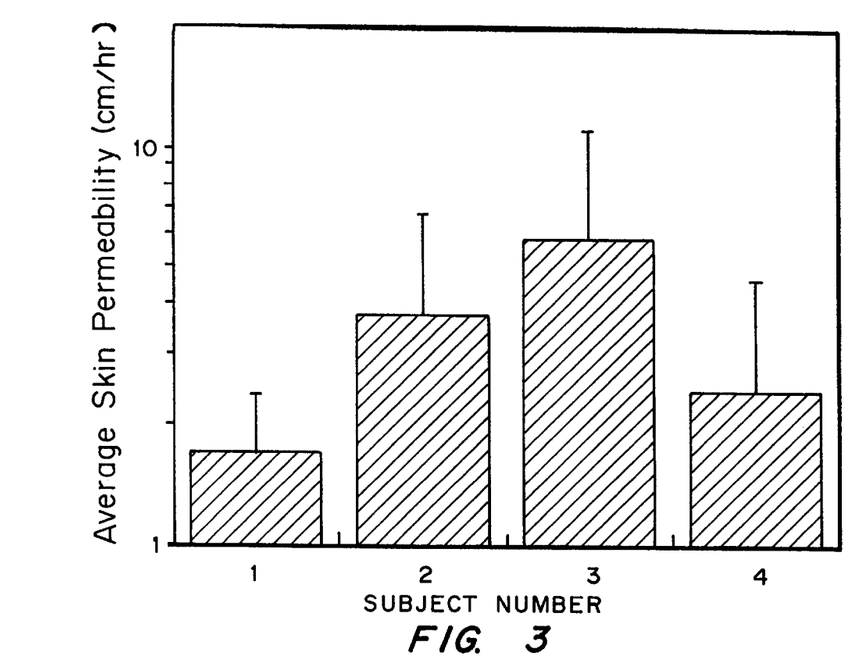
FIG. 3 is a graph comparing average skin to site variability of permeability (cm./hr.) within the same subjects. Three to five different locations between the elbow and the wrist on volar and dorsal forearm of four healthy human volunteers were tested. The date represents average and standard deviation of all sites on each subject.
Figure 4:
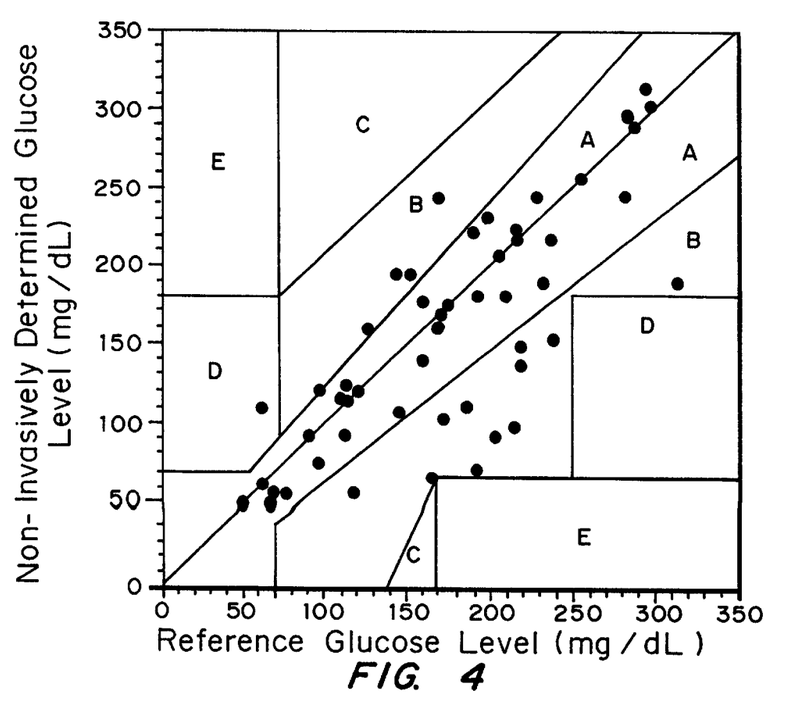
FIG. 4 is a graph comparing the statistical analysis of reference blood glucose levels (mg/dl) to sonophoretically measured glucose levels (mg/dl).

FIG. 2 is a comparison of venous blood glucose levels and non-invasively extracted glucose fluxes. For calibration, the first glucose flux value was divided by the appropriate serum glucose. The ratio was then used to calculate serum glucose from glucose flux for all subsequent measurements, (○) is blood concentration, (●) is glucose flux. Error bars indicate typical error in fluxes. The extracted glucose flux profile was shifted to a later time relative to the serum profile, suggesting a lag time of one sample period. The extracted glucose may be coming from capillaries under the surface of the skin located at the junction of the dermis and epidermis. The lag time observed between blood glucose measurements and ultrasound extracted glucose might therefore be related to the diffusion of capillary glucose across the epidermis and stratum corneum. The site to site variability (within the same subject) and subject to subject variability (averaged over a number of sites) of skin permeability were evaluated, and the results are shown in FIG. 3. Three to five different locations between the elbow and the wrist on volar and dorsal forearm of four healthy human volunteers were tested. The date represents average and standard deviation of all sites on each subject. The site to site variability (standard deviations on each bar in FIG. 3) is about the same as subject to subject variability (variations in the average values of bars in FIG. 3). This suggests the necessity of one point calibration between transdermal glucose flux and one blood sample, based on which subsequent blood glucose values may be predicted. Based on such a calibration, the relationship between transdermal glucose flux and blood glucose values was assessed using an error grid. The results are shown in FIG. 4. Predictions in zones A and B are clinically acceptable, while those in zones C, D, or E would lead to clinically significant errors. All but one of the 56 predictions based on transdermal glucose flux are in zones A and B.

Patients reported no pain during ultrasound application and no visible effect of the ultrasound on the skin could be detected. The results indicate that under the present conditions, low frequency ultrasound does not appear to induce damage to skin or underlying tissues.

The average transdermal glucose fluxes after ultrasound application are 25 fold higher than fluxes reported for the reverse iontophoresis technique, as reported by J. Tamada et al., Nature Med. 1:1198–1201 (1995).

EXAMPLE 2

Drug Delivery After Permeabilizing Ultrasound

Figure 5:
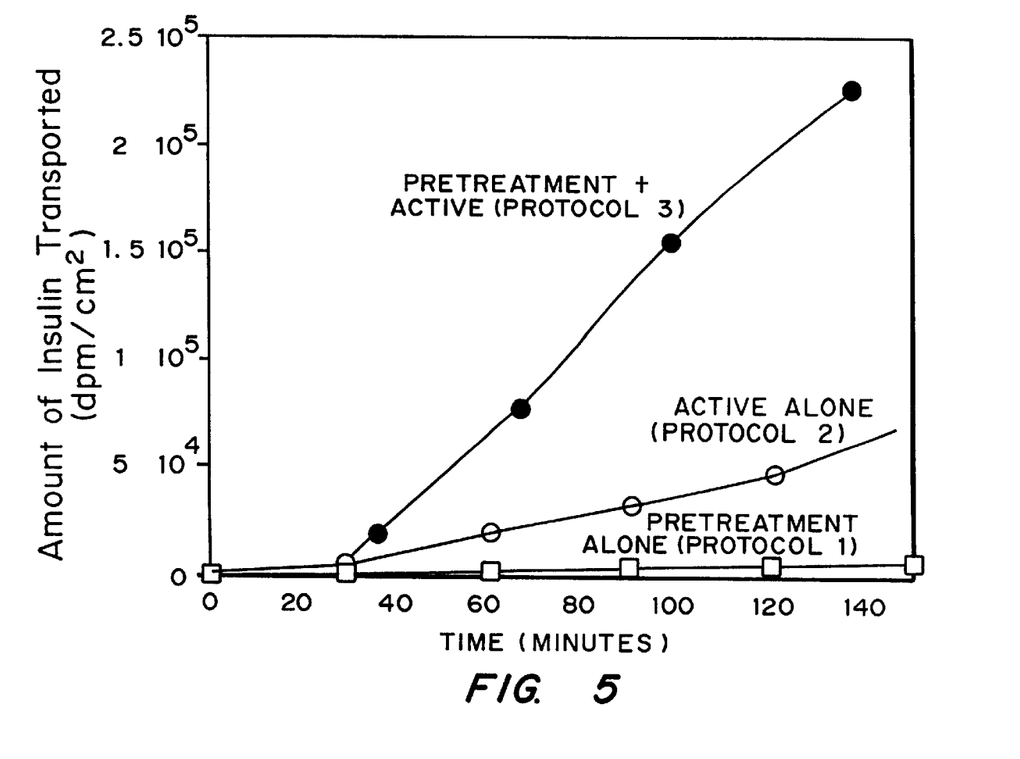
FIG. 5 is a graph illustrating insulin transport (at dpm/cm$^2$) over time (minutes) after ultrasound pretreatment alone (protocol 1), no pretreatment, with ultrasound application only during insulin application (○) (protocol 2), and ultrasound pretreatment and ultrasound application during insulin application (●) (protocol 3).

FIG. 5 illustrates a comparison of transdermal insulin delivery after the application of permeabilizing ultrasound alone (□protocol 1), with no pretreatment but with application of low frequency ultrasound during drug application (○-protocol 2), and with permeabilizing ultrasound along with transporting ultrasound (●-protocol 3).

Sprague Dawley rats were used for these studies. The hairless rats were anesthetized with a mixture of ketamine (60 mg/kg) and xylazine (10 mg/kg). After about an hour into anesthesia, a flanged glass cylinder (diameter 15 mm, height 2 cm) was glued onto the rat's back using a minimal amount of superglue or vacuum grease on the outer edges of the cylinder flange. The center of the cylinder was located about 3 cm from the rear end of the rat. This particular site was chosen to avoid application of ultrasound directly on a sharp bone close to the body surface, which otherwise might have caused damage to the blood capillaries near the edge of the bone. The cylinder was filed with phosphate buffered saline (PBS). Ultrasound (20 kHz, 7 W/cm$^2$, 5 sec pulses applied every 10 seconds) was applied by immersing the transducer in the solution. Rat skin conductivity was measured between the transducer and a subcutaneously implanted electrode. Ultrasound was stopped when the skin conductivity reached 3 kohms-cm$^2$. PBS was removed and replaced with a solution of radiolabeled insulin (about 10 μCi/ml). Urine was collected by placing a catheter in the rat's bladder. The concentration of insulin in the rat urine was measured using a scintillation counter (model 2000 CA, Packard). The results are shown in FIG. 5, white squares.

Protocol 2 consisted of no permeabilizing pretreatment, with low frequency ultrasound applied during insulin application. The same protocol as above was followed with the following exceptions: pretreatment of ultrasound was not done; radiolabeled insulin was applied along with ultrasound at 20 kHz, 1.5 W/cm$^2$, 100 msec pulses per second.

Protocol 3 was basically the combination of protocols 1 and 2 combined. Permeabilizing ultrasound was applied at 20 kHz, 7 W/cm$^2$, 5 sec pulses per 10 seconds. Transporting ultrasound was applied at 20 kHz, 1 W/cm$^2$, 5 sec pulses per 10 seconds.

Insulin transport by all three protocols was significant. Passive transport (without ultrasound pretreatment or application of ultrasound during drug application) was negligible and is not shown in the Figure.

EXAMPLE 3

Extraction and Detection of Glucose

Ultrasound was applied to the skin to increase its permeability and vacuum was used to extract interstitial fluid (ISF) into a gel containing glucose sensitive reagents. The change in the color of the gel can be monitored to determine the glucose concentration in the ISF.

In vitro experiments were performed using pig skin (Yorkshire) mounted on diffusion cells. The skin was harvested using a scalpel, immediately after sacrificing the animal and underlying fat was removed using a razor blade. Samples were cut into small pieces, and those with no visible imperfections (e.g. scratches or abrasions) were stored in a −80° C. freezer for up to 12 weeks. Just prior to an experiment, skin was thawed at room temperature and then immediately mounted onto a Franz diffusion cell. To ensure intact barrier function, only skin with initial resistivity 30 kΣcm$^2$ was used. The Franz cell is a vertical diffusion cell which consists of two compartments, the donor and the receiver compartments.

Skin was mounted on the diffusion cell and was exposed to ultrasound using 1% sodium lauryl sulfate as a coupling medium. Skin conductance was measured by placing two electrodes across the skin. The impedances were measured at two frequencies, 10 Hz and 1 kHz. The impedances measured at the frequencies differed by about 25 fold when skin was impermeable. Upon sonication, the difference between the impedances at two frequencies decreased. The decrease in the differential impedance increased with time. When the skin was highly permeable, the impedances at two frequencies differed only by approximately 20%. SLS was removed from the chamber and the chamber was dried.

A gel was prepared by mixing glucose reagent from the Sigma glucose detection kit #315 (10% by weight) in a solution of polyvinyl alcohol (20% by weight) in phosphate buffered saline (PBS). The solution was poured into a tray to form a thin film and was kept in the freezer (−20° C.) overnight to allow crosslinking between polyvinyl alcohol molecules. The resulting gel is transparent in the absence of glucose. It changes to red when it comes in contact with glucose in accordance with the following reaction:

Glucose+$H_2O$+$O_2$+Glucose oxidase→Gluconic acid+$H_2O_2$ $H_2O_2$+4 Aminoantipyrine+

The gel was punched into disks and a disk placed on the skin that was permeabilized by ultrasound using the same conditions as in Example 1, but using pigskin. Vacuum was applied. The gel changed its color to red within five minutes. This gel can be used as a qualitative indicator of glucose. In combination with a spectrophotometric device, this method could also be used for quantitative detection of glucose.

EXAMPLE 4

Ultrasound Enhancement of Analyte Transport across Human Cadaver Skin.

Permeability experiments were performed in vitro using human cadaver skin (obtained from local hospitals and the National Disease Research Institute). The skin was heat stripped by keeping the full-thickness skin in water at 60° C. for two minutes followed by removal of the epidermis which was then stored at 4° C. in a humidified chamber for up to 2 weeks and mounted on a Franz diffusion cell (Crown Glass Co., FDC 400). The epidermis was supported by a nylon mesh (Tetko, Inc.) to avoid damage due to possible mechanical oscillations upon ultrasound application. The receiver compartment was filled with phosphate buffer saline (PBS, phosphate concentration of 0.01 M, NaCl concentration of 0.137 M) (Sigma Chemicals Co.) except for calcium transport experiments, where it was filled with deionized water. Prior to each experiment, the electrical resistance of the skin was measured to ensure its integrity. The skin was considered damaged if the initial specific skin resistance was less than 10 kohm-$cm^2$. The donor solution was filled with calf seurum (Sigma Chemicals). Typical concentrations of analytes in the serum were glucose 80 mg/dL, urea 16 mg/dL and calcium=5 mg/dL. $^3$H-theophylline was added to the donor compartment at a concentration of 0.5 $\mu$Ci/mL. Experiments were also performed using $^{14}$C glucose. In these experiments the donor compartment was filled with 0.5 $\mu$Ci/ml solution of $^{14}$C glucose (New England Nuclear) in PBS. Samples were taken from the donor and the receiver compartments. Concentration of glucose in the diffusion cell compartments was detected using two methods. When $^{14}$C labeled glucose was used, the concentration was measured by a scintillation counter (Packard model 2000 CA). The concentrations of unlabelled glucose, urea and calcium were measured using spectrophotometric detection kits (#315 for glucose, #586 for calcium and #535 for urea, all from Sigma Chemicals). The reagent to sample ratio in these kits were modified to a value of 2 for glucose and calcium, and 10 for urea to lower the concentration detection limit. Theophylline concentration in the diffusion cell compartments was measured using a scintillation counter (Packard MODEL CA). Ultrasound was applied using a sonicator (VCX 400, Sonics and Materials) operating at a frequency of 20 kHz, tip displacement of 2 $\mu$m, continuous mode, for 10 minutes.

Figure 6:
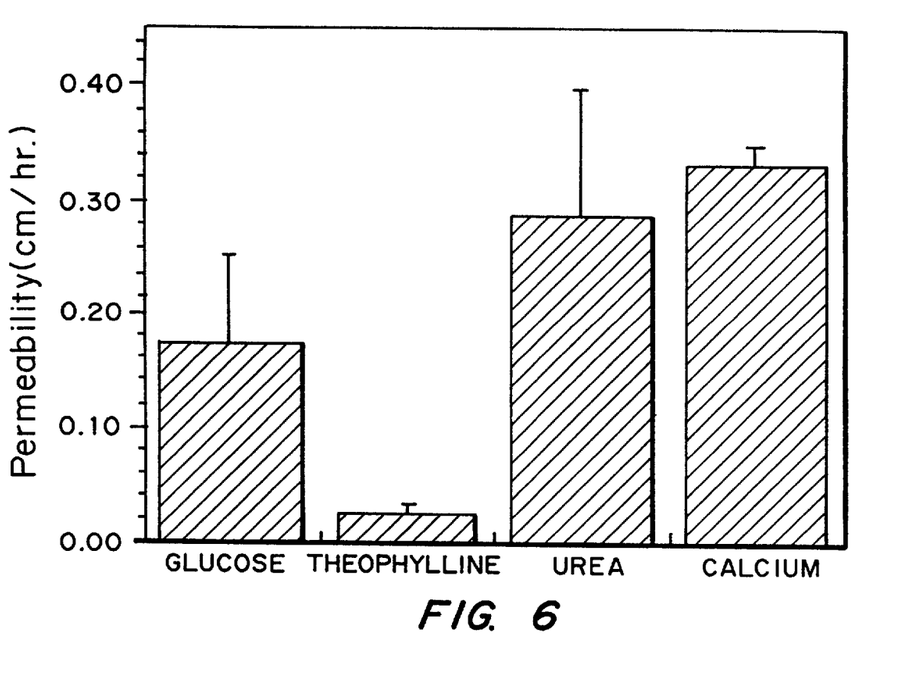
FIG. 6 is a graph of permeability as measured by the transport (cm/hr) in vitro of various analytes across human cadaver skin after continuous application of ultrasound. The concentrations of unlabelled glucose, urea, and calcium were measured using spectrophotometric detection kits (315 for glucose, 586 for calcium and 535 for urea). Theophylline concentration in the diffusion cell compartments was measured using a scintillation counter (Packard MODEL CA). Ultrasound was applied using a sonicator (VCX 400, Sonics and Materials) operating at a frequency of 20 KHz, tip displacement of 2 μm, continuous mode, for 10 minutes.

Transdermal extraction of all molecules studied was observed as shown in (FIG. 6), with permeabilities several orders of magnitude higher than those observed by passive diffusion across skin. For example, passive skin permeability of glucose is about $3\times10^4$ cm/hr, compared to $17\times10^{-2}$ cm/hr following ultrasound application (570 fold increase). Control experiments were performed to ensure that the extracted analytes originated from the donor compartment and not skin itself. In the experiments the donor compartment was filled with phosphate buffered saline instead of serum and ultrasound extraction was performed. No significant amount of glucose (<0.04%), urea (<0.3%), or calcium (<1%) was found in the receiver compartment after 10 minutes of ultrasound exposure. This was further confirmed by radiolabeled glucose studies.

EXAMPLE 5

In Vivo Analyte Extraction After Permeabilizing Ultrasound

All animal procedures were performed using institutional approved protocols. Rats (Sprague Dawley (SD), either sex) were anesthetized with a mixture of ketamine (60 mg/kg) and xylazine (10 mg/kg) injected i.p. or i.m. After anesthesia was confirmed, a flanged glass cylinder (Crown Glass Co., diameter 15 mm, height 2 cm) was glued on the rat's shaved lateral flank using a minimal amount of cyanoacrylate adhesive (Permabond International or Vet Bond) on the outer edge of the flange. The chamber was filled with 2 mL of PBS or deionized water. At the end of one hour, ultrasound (20 kHz, 11 $\mu$m, pulsed 5 sec. on/5 sec. off) was applied by immersing the transducer in the donor solution for 2 minutes. At the end of 2 minutes the contents of the chamber were removed and replaced (after rinsing) with 2 ml of fresh buffer (PBS). Ultrasound displacement was lowered to 1 $\mu$m for an additional 15 minutes, after which the chamber content was replaced by fresh PBS (the removed volume was used for analyte detection). The ultrasound procedure was repeated for the length of the experiments (3 hours). At the end of the experiment, the rat was euthanasized and the skin exposed to ultrasound was excised and stored in 10% formalin for histologic studies.

Figure 7:
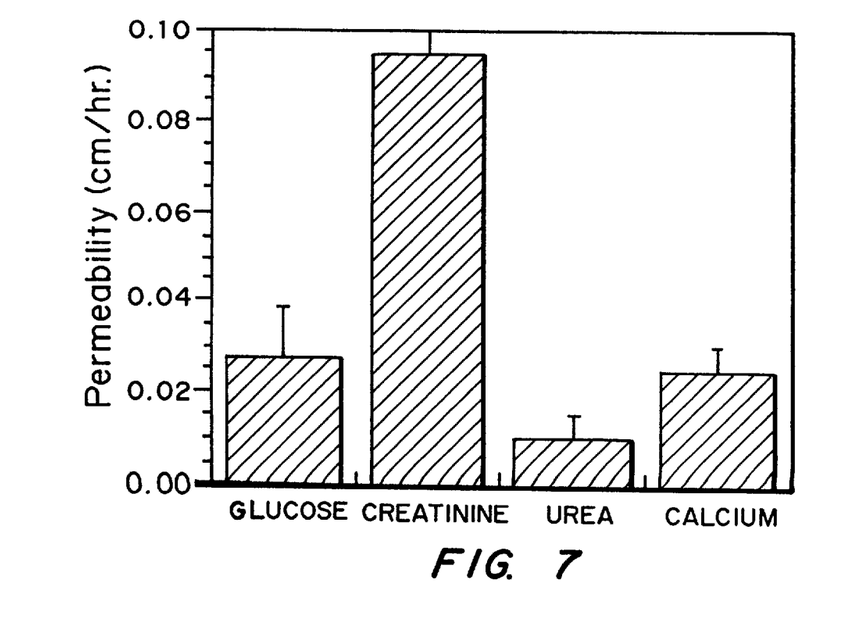
FIG. 7, is a graph of permeability (cm/hr) as measured by transport of various analytes across rat skin in vivo. Permeabilizing ultrasound was applied (20 kHz, tip displacement of 2 μm, continuous mode) for 2 minutes.

Extraction of glucose, calcium, urea, and creatinine was noted following ultrasound application (FIG. 7), with permeabilities significantly greater than observed by passive diffusion. For example, glucose permeability, which was undetectable without any treatment, increased to $2.6\times10^-2\pm1.1\times10^{-2}$ cm/hr after ultrasound irradiation. The significance of each step in the protocol, that is, hydration, skin permeabilization using ultrasound, and extraction using ultrasound (or vacuum) to the enhanced transport was evaluated. The skin permeability to glucose was undetectable before hydration, $4\times10^{-4}\pm3\times10^{-4}$ cm/hr immediately after hydration, $3.4\times10^{-3}\pm2.5\times10^{-3}$ cm/hr immediately after ultrasonic skin permeabilization and $2.6\times10^{-2}$11 $1\times10^{-2}$ cm/hr during ultrasonic extraction, or $3.4\times10^{-2}$35 $2.5\times10^{-2}$ during vacuum-based extraction. Time variation of these permeabilities over a period of three hours was within 10%, suggesting that skin permeability of a given site was maintained over at least three hours.

EXAMPLE 6

Correlation (in vivo) of Non-invasive Determination of Glucose with Blood Glucose Measurements.

To determine if the amount of glucose extracted represented meaningful physiologic determination of venous blood glucose, experiments were performed in which rats were injected via the jugular vein with two boluses of radiolabeled glucose 85 minutes apart. SD rats were anesthetized as described above. After anesthesia was confirmed, the jugular vein was catheterized as described in H. B. Waynforth and P. A. Flecknell, Experimental and surgical technique in the rat, $2^{nd}$ Ed. Academic Press, London, pp 215–222, (1992). The first injection of radiolabled glucose (200 $\mu$Ci) was immediately after two minutes of ultrasound exposure, the second injection (200 µCi) was 85 minutes later. Extraction was performed as described in Example 5.

Figure 8:
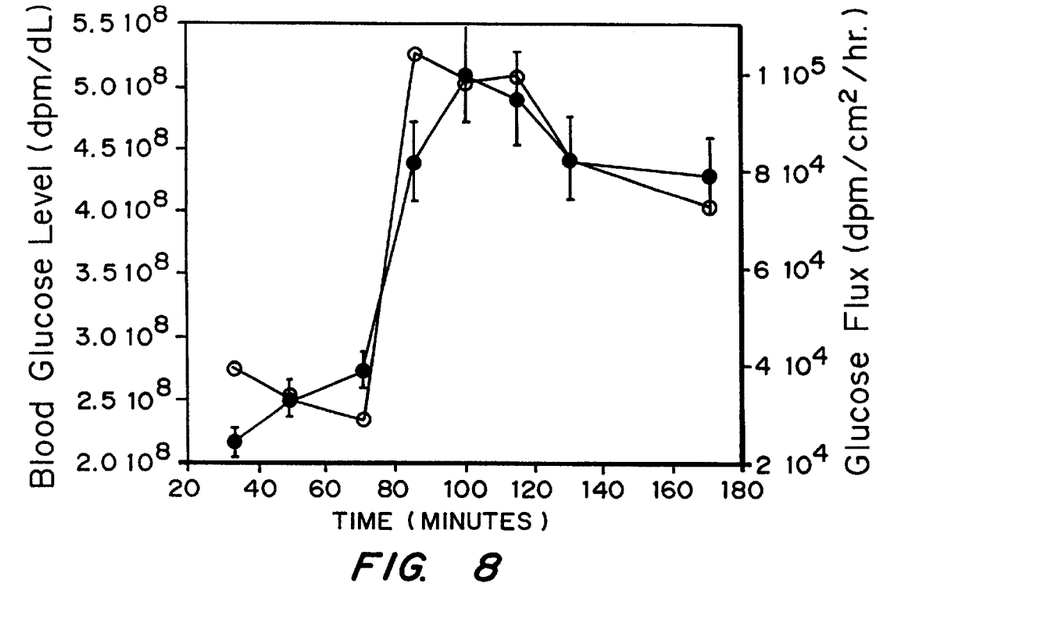
FIG. 8, is a graph of blood glucose levels (dpm/dl) and glucose flux (dpm/cm$^2$/hr) in rats, over a 180 minute period of time, where (○) is blood concentration and (●) is glucose flux. Error bars indicate typical error in fluxes.
Figure 9:
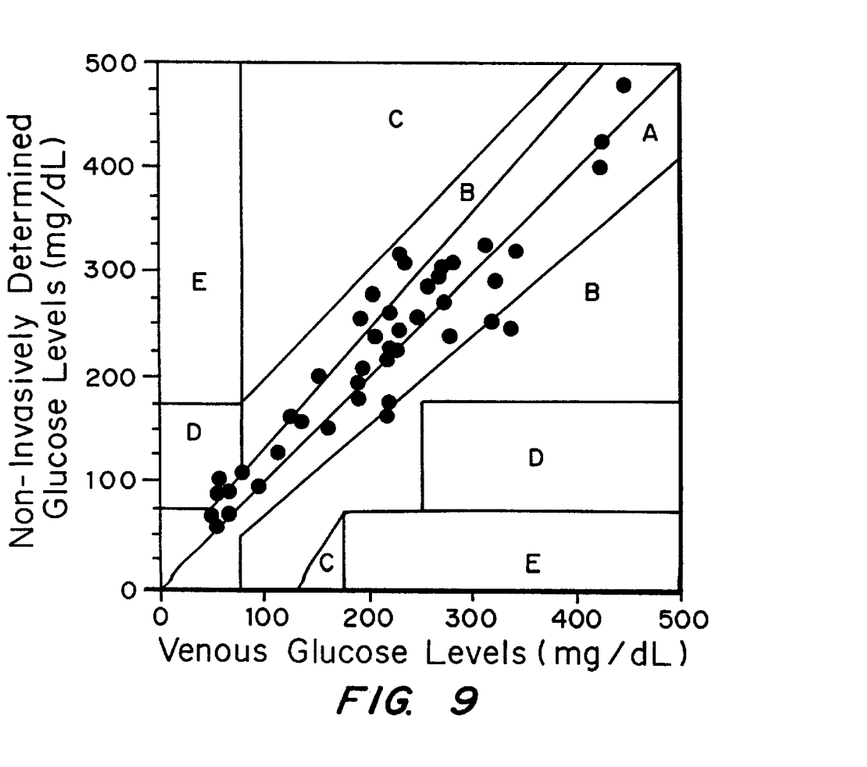
FIG. 9 is an error grid analysis comparing the reference serum glucose and the measured glucose (mg/dl) calculated from the measured noninvasive glucose flux into five zones. Values in zones A and B are clinically acceptable. For calibration the third glucose flux value was divided by the third serum glucose. The ratio was then used to calculate serum glucose from glucose flux for all subsequent measurements.

The curves for the non-invasively extracted glucose flux followed the blood glucose concentration as shown in FIG. 8. FIG. 9 illustrates the comparison of blood glucose values predicted based on transdermal flux and those directly measured using blood samples. FIG. 9 indicates a good correlation for both hypoglycemic and hyperglycemic ranges (about 0.94). Another criterion for accuracy is the mean absolute error between the reference and calculated glucose value defined by: absolute error=[(serum glucose−calculated glucose)/serum glucose]×100. A mean absolute error of 13% was obtained for all measurements (n=45). Histologic studies were performed on rat skin samples exposed to multiple ultrasound applications under identical conditions used for glucose extraction. No physical damage was noted in any of the histologic specimens. Furthermore, the regions of rat epidermis exposed to ultrasound were intact and showed no abnormalities.

Publications cited herein and the material for which they are cited are specifically incorporated by reference. Modifications and variations of the present invention will be obvious to those skilled in the art from the foregoing detailed description and are intended to be encompassed by the following claims.

What is claimed is:

1. A method for enhanced transport of a molecule into or through skin, comprising the steps:

permeabilizing the skin by applying low frequency ultrasound to the area of the skin where permeabilization is desired, wherein the frequency of the ultrasound is between about 20 kHz and 1 MHz;

subsequently applying a driving force to extract analyte molecules through or to deliver drug molecules into the skin over a period of time following the permeabilization without repermeabilizing the skin.

2. The method of claim 1 further comprising repeating the permeabilizing step between 1 and 10 hours later.

3. The method of claim 1, further comprising applying a chemical enhancer.

4. The method of claim 1 wherein the driving force is selected from the group consisting of suction, osmotic pressure gradient, concentration gradient, capillary forces, convection, iontophoresis, electroporation, magnetic fields, and mechanical pressure.

5. The method of claim 1, further comprising the step of applying a cavitation enhancer to the skin or in a coupling medium.

6. The method of claim 1, wherein the step of permeabilizing the skin is effective to permeabilize the skin for at least 30 minutes.

7. The method of claim 1 further comprising applying surfactant to the skin or in a coupling medium at the time of permeabilization.

8. The method of claim 1, further comprising analyzing the analyte concentration at the time of extraction or the concentration of the drug or marker to be transported.

9. The method of claim 1, further comprising providing a reservoir into which analyte molecules are extracted.

10. The method of claim 1, further comprising providing a reservoir for delivery of the drug molecules.

11. The method of claim 1 further comprising providing a transdermal patch for delivery of molecules to be transported or collection of analyte to be extracted.

12. The method of claim 1, further comprising the step of determining the degree of permeabilization.

13. The method of claim 1 further comprising measuring the concentration of a molecule present in interstitial fluid that remains relatively constant, for use in determining the degree of permeabilization or calibrating the concentration of molecules to be transported.

* * * * *